(12) United States Patent
Kasibhatla et al.

(10) Patent No.: US 7,553,979 B2
(45) Date of Patent: Jun. 30, 2009

(54) HSP90-INHIBITING ZEARALANOL COMPOUNDS AND METHODS OF PRODUCING AND USING SAME

(75) Inventors: Srinivas R. Kasibhatla, San Diego, CA (US); Jean-Yves Le Brazidec, San Diego, CA (US); Sean Konrad McHugh, Iingleside, IL (US); Marcus F. Boehm, San Diego, CA (US)

(73) Assignee: Conforma Therapeutics Corporation, San Diego, CA (US)

( * ) Notice: Subject to any disclaimer, the term of this patent is extended or adjusted under 35 U.S.C. 154(b) by 360 days.

(21) Appl. No.: 10/496,401

(22) PCT Filed: Nov. 8, 2002

(86) PCT No.: PCT/US02/35938

§ 371 (c)(1),
(2), (4) Date: Jun. 9, 2005

(87) PCT Pub. No.: WO03/041643

PCT Pub. Date: May 22, 2003

(65) Prior Publication Data

US 2005/0256183 A1   Nov. 17, 2005

Related U.S. Application Data

(60) Provisional application No. 60/337,919, filed on Nov. 9, 2001.

(51) Int. Cl.
*C07D 313/00* (2006.01)
*A01N 43/02* (2006.01)

(52) U.S. Cl. ...................... 549/269; 514/450

(58) Field of Classification Search ................. 549/269
See application file for complete search history.

(56) References Cited

U.S. PATENT DOCUMENTS

| | | | | |
|---|---|---|---|---|
| 3,196,019 A | * | 7/1965 | Andrews et al. | ............ 514/450 |
| 3,239,341 A | | 3/1966 | Hodge et al. | |
| 3,239,342 A | | 3/1966 | Hodge et al. | |
| 3,239,345 A | | 3/1966 | Hodge et al. | |
| 5,674,892 A | * | 10/1997 | Giese et al. | ................. 514/450 |
| 6,635,671 B1 | * | 10/2003 | Kastelic et al. | ............. 514/450 |

FOREIGN PATENT DOCUMENTS

| | | |
|---|---|---|
| WO | WO 00/06143 | 2/2000 |
| WO | WO 02/48136 A1 | 6/2002 |

OTHER PUBLICATIONS

Bass et al. Journal of the Chemical Society, Perkin Transactions 1, Organic and Bioorganic Chemistry, (1981), 1, 124-31.*
Sakamoto et al. STN Accession No. 174572, Document No. 28511a, 28514a, Abstract of Tetrahedron Letters, (2001), 42 (43), 7633-7636.*
Patani et al. Chemical Reviews, 1996, 96, 3147-3176, pp. 3155 and 3156.*
Shier et al. Toxicon, 2001, 1435-1438.*
Clarke, Hilakivi L. et al. "Prepubertal exposure to zearalenone or genistein reduces mammary tumorigenesis" British Journal of Cancer (1999) 80(11), pp. 1682-1688.
Furstner, Alois et al. "Macrocycles by Ring-Closing-Metathesis, XI: Syntheses of (R)-(+)-Lasiodiplodin, Zeranol and Truncated Salicylihalamides" Tetrahedron 55 (1999) pp. 8215-8230.

* cited by examiner

*Primary Examiner*—D. Margaret Seaman
*Assistant Examiner*—Nizal S Chandrakumar
(74) *Attorney, Agent, or Firm*—Finnegan Henderson Farabow Garrett & Dunner, LLP

(57) ABSTRACT

Zearalanol compounds are described and demonstrated or predicted to have utility as Heat Shock Protein 90 (HSP90) inhibiting agents in the treatment and prevention of various disorders. Methods of synthesis and use of such compounds are also described and claimed.

11 Claims, 1 Drawing Sheet

HSP90-INHIBITING ZEARALANOL COMPOUNDS AND METHODS OF PRODUCING AND USING SAME

RELATED APPLICATION

This application claims priority to and incorporates by reference in its entirety Kasibhatla et al., U.S. Provisional Patent Application Ser. No. 60/337,919, entitled HSP90-inhibiting Zearalanol Compounds and Methods of Producing and Using Same, filed Nov. 9, 2001.

FIELD OF THE INVENTION

The application relates to the synthesis and utility of radicicol-like zearalanol compounds.

BACKGROUND

The following description includes information that may be useful in understanding the present invention. It is not an admission that any of the information provided herein is prior art or relevant to the presently claimed inventions, or that any publication specifically or implicitly referenced is prior art.

HSP90s are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J., 1999, TIBS, 24:136-141; Stepanova, L. et al., 1996, Genes Dev. 10:1491-502; Dai, K. et al., 1996, J. Biol. Chem. 271: 22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see, e.g., Caplan, A., Trends in Cell Biol., 9: 262-68 (1999). HSP90s have also been implicated in various cellular proliferative disorders, affected cells of which appear to be hypersensitive to HSP90 inhibitors relative to normal cells.

Various small molecule compounds, including ansamycin antibiotics derived from *Streptomyces hygroscopicus* are known to inhibit HSP90s. These antibiotics, e.g., herbimycin A (HA) and geldanamycin (GM), as well as other HSP90 inhibitors such as radicicol, bind tightly to an N-terminus pocket in HSP90 (Stebbins, C. et al., 1997, *Cell*, 89:239-250). This pocket is highly conserved and has weak homology to the ATP-binding site of DNA gyrase (Stebbins, C. et al., supra; Grenert, J. P. et al., 1997, *J. Biol. Chem.*, 272:23843-50). Further, ATP and ADP have both been shown to bind this pocket with low affinity and to have weak ATPase activity (Proromou, C. et al., 1997, *Cell*, 90:65-75; Panaretou, B. et al., 1998, *EMBO J*, 17: 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T., H. et al., 1999, *Proc. Natl. Acad. Sci. USA* 96:1297-302; Schulte, T. W. et al., 1995, *J. Biol. Chem.* 270:24585-8; Whitesell, L., et al., 1994, *Proc. Natl. Acad. Sci. USA* 91:8324-8328). Ansamycins have also been demonstrated to inhibit the ATP-dependent release of chaperone-associated protein substrates (Schneider, C., L. et al., 1996, *Proc. Natl. Acad. Sci. USA*, 93:14536-41; Sepp-Lorenzino et al., 1995, *J. Biol. Chem.* 270:16580-16587). In either event, the substrates are degraded by a ubiquitin-dependent process in the proteasome (Schneider, C., L., supra; Sepp-Lorenzino, L., et al., 1995, *J. Biol. Chem.*, 270:16580-16587; Whitesell, L. et al., 1994, *Proc. Natl. Acad. Sci. USA*, 91:8324-8328).

This substrate destabilization occurs in tumor and non-transformed cells alike and has been shown to be especially effective on a subset of signaling regulators, e.g., Raf (Schulte, T. W. et al., 1997, Biochem. Biophys. Res. Commun. 239:655-9; Schulte, T. W., et al., 1995, J. Biol. Chem. 270:24585-8), nuclear steroid receptors (Segnitz, B., and U. Gehring. 1997, J. Biol. Chem. 272:18694-18701; Smith, D. F. et al., 1995, Mol. Cell. Biol. 15:6804-12), v-src (Whitesell, L., et al., 1994, Proc. Natl. Acad. Sci. USA 91:8324-8328) and certain transmembrane tyrosine kinases (Sepp-Lorenzino, L. et al., 1995, J. Biol. Chem. 270:16580-16587) such as EGF receptor (EGFR) and Her2/Neu (Hartmann, F., et al., 1997, Int. J. Cancer 70:221-9; Miller, P. et al., 1994, Cancer Res. 54:2724-2730; Mimnaugh, E. G., et al., 1996, J. Biol. Chem. 271:22796-801; Schnur, R. et al., 1995, J. Med. Chem. 38:3806-3812), CDK4, and mutant p53. Erlichman et al., Proc. AACR (2001), 42, abstract 4474. The ansamycin-induced loss of these proteins leads to the selective disruption of certain regulatory pathways and results in growth arrest at specific phases of the cell cycle (Muise-Heimericks, R. C. et al., 1998, J. Biol. Chem. 273:29864-72), and apoptosis, and/or differentiation of cells so treated (Vasilevskaya, A. et al., 1999, Cancer Res., 59:3935-40).

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating ischemia, and agents useful in promoting nerve regeneration (See, e.g., Rosen et al., WO 02/09696; PCT/US01/23640; Degranco et al., WO 99/51223; PCT/US99/07242; Gold, U.S. Pat. No. 6,210,974 B1). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis may be treatable. (Strehlow, WO 02/02123; PCT/US01/20578).

HSP90 inhibitors thus hold great promise for the treatment and/or prevention of many types of cancers and proliferative disorders. It is an object of the invention to identify new and/or existing compounds that can function as HSP90 inhibitors. In particular, the invention relates to zearalanol compounds other than radicicol and known analogs thereof, and to methods of synthesis and use of such compounds. Apart from radicicol, zearalanol compounds have not been studied as HSP90 inhibiting agents, but rather as other types of agents, e.g., anabolic agents (see, e.g., U.S. Pat. No. 3,196, 019), and agents that destabilize mRNA (see, e.g., WO 00/38674). Further, the majority of zearalanol compounds are naturally occurring and present challenges by way of fermentation and biochemical purification. Id.

There is a need for new HSP90 inhibitors, especially synthetic zearalanol compounds.

SUMMARY OF THE INVENTION

Applicants herein describe HSP90-inhibiting activity of a variety of commercially available non-radicicol zearalanol-type compounds and provide synthesis schemes for these and a variety of analogous compounds. These compounds bode utility for the prevention and/or treatment of various proliferative disorders that are HSP90-dependent, e.g., breast cancer, prostate cancer, etc.

In a first aspect, the invention features a zearalanol analog, preferably synthetic, of formula I, II, III or IV

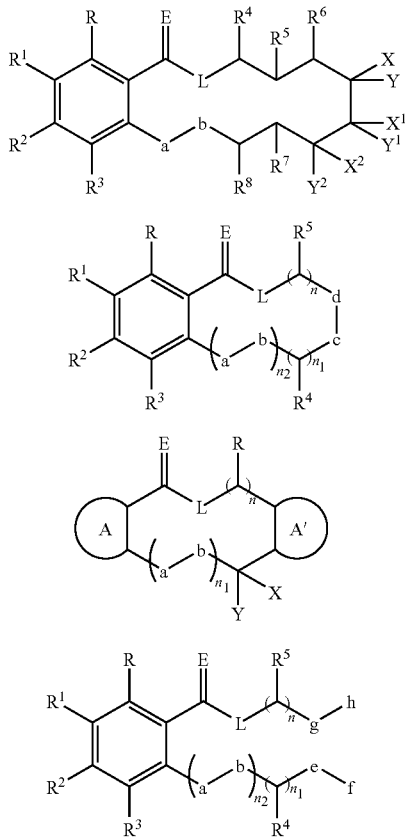

wherein

R, $R^1$, $R^2$ and $R^3$ are selected from the group: $NR^9{}_2$, $NHSO_2R^{10}$, $OR^{11}$, $SR^{11}$, optionally substituted lower alkyl, $NH_2$, H, halo and perhaloalkyl;

$R^4$, $R^5$, $R^6$, $R^7$ and $R^8$ are selected from the group: $NR^9{}_2$, $NHSO_2R^{10}$, $OR^{11}$, $SR^{11}$, optionally substituted lower alkyl, $CON(R^{12})_2$, $=O$, $NH_2$, H, halo and perhaloalkyl;

$R^9$ is selected from H, optionally substituted alkyl and $C(O)NR^4{}_2$;

$R^{10}$ is optionally substituted alkyl;

$R^{11}$ is selected from H, optionally substituted alkyl, and $C(O)NR^4{}_2$;

$R^{12}$ is selected from H and optionally substituted alkyl;

E is selected from $NR^{13}$, O and S;

$R^{13}$ is selected from optionally substituted alkyl, O-alkyl and O-aryl;

L is selected from $CR^{12}{}_2$, $NR^{14}$, O and S;

$R^{14}$ is selected from H and optionally substituted alkyl or aryl;

X and Y each independently can be H, $NR^9{}_2$, $OR^{11}$ and $SR^{11}$ or together can be $=O$, $=CR^{12}{}_2$;

$X^1$ and $Y^1$ each independently can be H, $NR^9{}_2$, $OR^{11}$ and $SR^{11}$ or together can be $=O$, $=CR^{12}{}_2$;

$X^2$ and $Y^2$ each independently can be H, $NR^9{}_2$, $OR^{11}$ and $SR^{11}$ or together can be $=O$, $=CR^{12}{}_2$;

X and $X^1$ together can be an epoxide or an optionally substituted aziridine or optionally substituted cyclopropane.

$X^1$ and $X^2$ together can be an epoxide or an optionally substituted aziridine or optionally substituted cyclopropane.

-a-b- is $CHR^{15}$—$CHR^{16}$ or Z-CHR or a triple or double carbon-carbon bond;

Z is $NR^{12}$, O or S;

-c-d- is —$CHR^{15}$—$CHR^{16}$ or a double bond;

$R^{15}$ and $R^{16}$ are each independently the same as R or together can be an aziridine or an epoxide or a cyclopropane;

-e-f- is $CHR^{15}$—$CH_2R^{16}$ or a triple bond or a double bond;

$R^{15}$ and $R^{16}$ each independently can be the same as R or together can be an aziridine or an epoxide or a cyclopropane;

-g-h- is $CHR^{15}$—$CH_2R^{16}$ or a triple bond or a double bond;

$R^{15}$ and $R^{16}$ each independently can be the same as R or together can be an aziridine or an epoxide or a cyclopropane;

n is an integer from 1 to 5;

$n_1$ is an integer from 1 to 5;

$n_2$ is an integer from 1 to 5;

A and A' are independently selected from aromatic and heteroaromatic rings, e.g., aryl, benzimidazol, imidazol, indol, indazol, pyrol, and pyrazol.

A proviso may be that the synthetic compounds claimed are not disclosed elsewhere or otherwise known. Some zearalanaol analogs, not all synthetic, may be found in U.S. Pat. No. 3,196,019, WO 00/38674, Furstner et al., Tetrahedron 55: 8215-8230 (1999), and EP 0606044.

A related aspect entails synthesis schemes for zearalanol compounds that make use of ring-closing-metathesis (RCM). In that aspect, the proviso can be more limited, e.g., to exclude only those compounds known to be so synthesized, e.g., the Furstner et al., Tetrahedron 55: 8215-8230 (1999) compounds shown in the following:

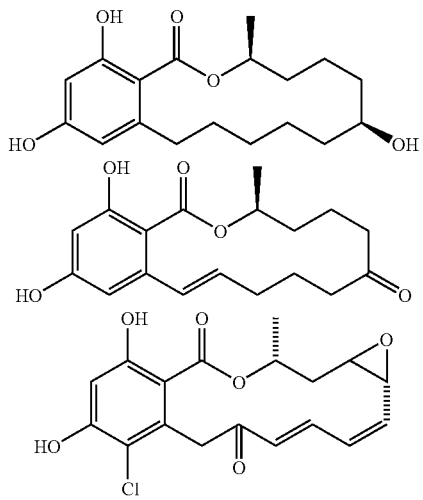

In some embodiments, the compound preferably has formula I.

In some embodiments, the compound preferably has formula II.

In some embodiments, the compound preferably has formula III.

In some embodiments, the compound preferably has formula IV.

In some embodiments, the compound is synthetic. The term "synthetic" contrasts with a natural compound that is merely isolated or purified from nature. The term also embraces semi-synthetic compounds wherein a naturally occurring precursor compound is subsequently modified by man using a known technique to form a synthetic product that has one or more synthetic components. The synthetic product may have a naturally-occurring counterpart in nature but is itself man-made beyond simple purification/isolation.

In another aspect, the invention features pharmaceutical compositions containing one or more of the compounds described for the preceding aspect, including or excluding provisos. These typically include, in addition to the compound of the invention or prodrug thereof, one or more of a pharmaceutically acceptable salt, carrier or excipient. "Prodrugs" are derivative compounds that are derivatized by the addition, e.g., an amide, or phosphorus group to endow greater solubility to the compound desired to be delivered. Once in the body, the prodrug is typically acted upon by an enzyme, e.g., an esterase, amidase, or phosphatase, to generate the active compound. Those of ordinary skill in the art have the knowledge and means to accomplish derivatization to this end without undue experimentation.

In another aspect, the invention features methods of inhibiting an HSP90 molecule with a compound selected from the first aspect, including or excluding the proviso. HSP90 proteins are highly conserved in nature (see, e.g., NCBI accession #'s P07900 and XM 004515 (human α and β HSP90, respectively), P11499 (mouse), AAB2369 (rat), P46633 (chinese hamster), JC1468 (chicken), AAF69019 (flesh fly), AAC21566 (zebrafish), AAD30275 (salmon), 002075 (pig), NP 015084 (yeast), and CAC29071 (frog). Grp94 and Trap-1 are related molecules falling within the definition of an HSP90-as used herein. There are thus many different HSP90s, all with anticipated similar effect and inhibition capabilities. The HSP90 inhibitors of the invention may be specifically directed against an HSP90 of the specific host patient or may be identified based on reactivity against an HSP90 homolog from a different species, or an HSP90 variant. The methods feature contacting a cell having an HSP90 with a pharmaceutically effective amount of a compound or pharmaceutical composition according to any one of the preceding aspects. The cell is preferably a mammalian cell, and more preferably a human cell, although any cell-type from any species that contains an HSP90, including non-mammalian lines, is contemplated for the invention. The method can be "in vitro", e.g., contacting a cell line in culture, or else can be "in vivo", e.g., contacting a cell inside a live organism. One type of in vivo administration is made "in situ", or directly to a specific cell or group of cells within an organism, e.g., intratumorally. "Ex vivo" procedures are also envisioned wherein the cells are first removed from a patient, treated by contacting them with the compounds or compositions of the invention, and then administered back to a patient or "the" patient. The compounds and compositions can be administered in a variety of ways, e.g., intravenously, parenterally, orally, bucally, intramuscularly, sublingually, topically, by aerosol, subcutaneously, intramuscularly, intraperitoneally, rectally, vaginally, intratumorally, or peritumorally.

In some preferred embodiments, the compounds or compositions are administered to cancer cells, e.g., Her2/neu breast cancer cells.

In some preferred embodiments, the compounds and compositions of the invention have a differential IC50 between cells characterized by a proliferative disorder and normal cells such that it is possible to administer concentrations of the compounds or pharmaceutical compounds of the invention such as to preferentially effect cells characterized by the proliferative disorder as opposed to normal cells. Methods of making the IC50 determination and supplying an appropriate amount to the cell or cells of interest to selectively achieve the desired effect are also embraced within the spirit of the invention.

In another aspect the compounds, compositions, and methods of the previous aspects employ compounds manufactured according to the following synthetic schemes:

Compound I:

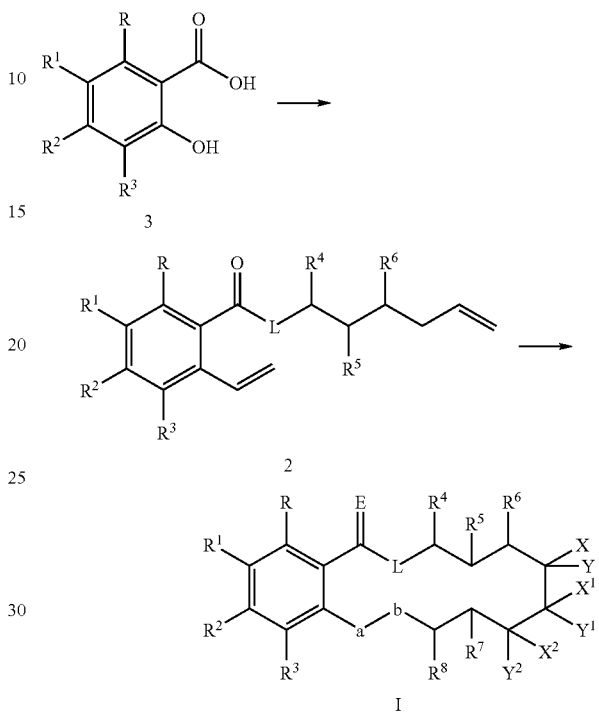

Compound II:

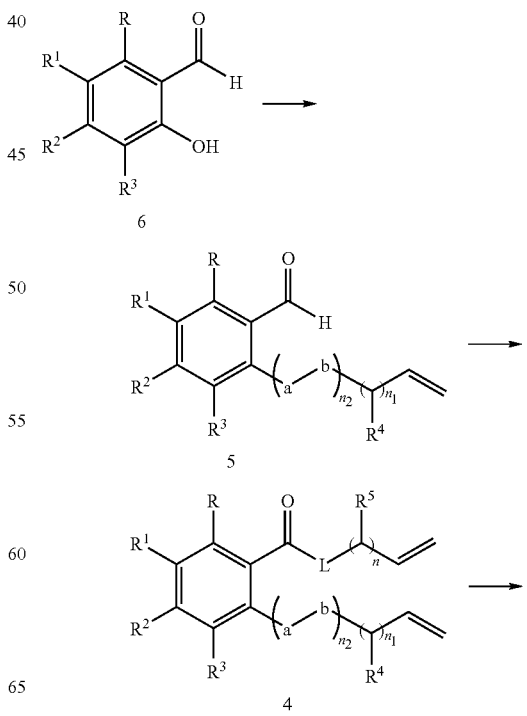

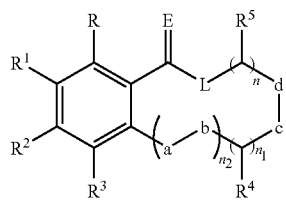

II

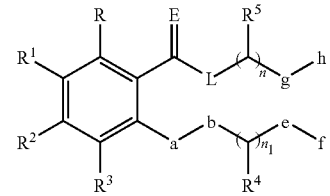

IV

Compound III:

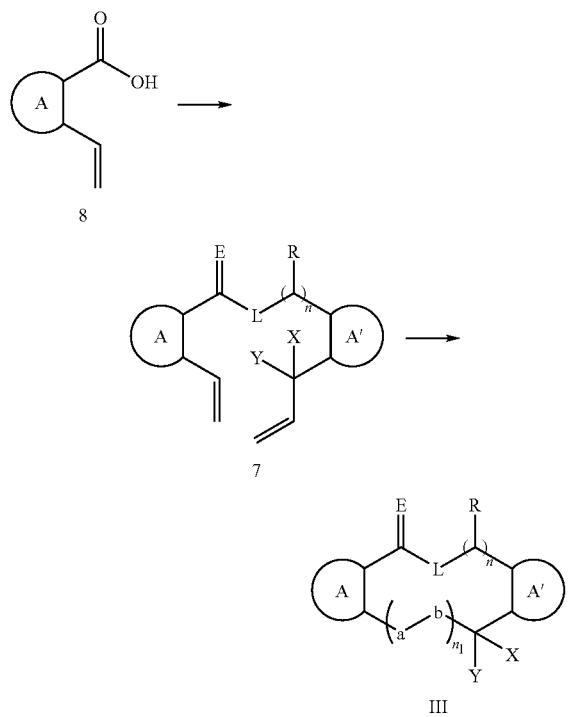

Compound IV:

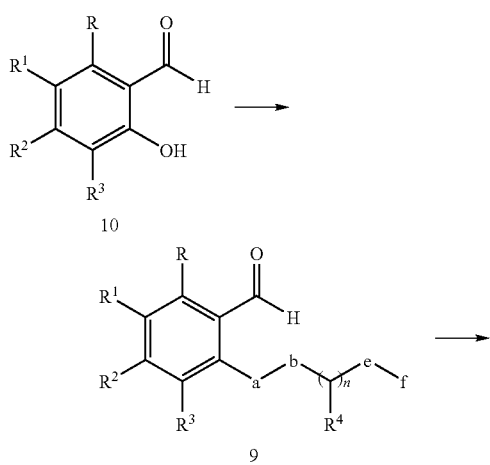

One of ordinary skill will appreciate that numerous chiral centers exist that can result in a number of stereochemically distinct forms of the final compound. Techniques exist to control or select for the formation and maintenance the stereochemical integrity of stereogenic centers of final products during their synthesis and/or isolation and purification.

In some aspects, the compounds or compositions are administered to treat or prevent a cancer, e.g., a breast cancer, melanoma, lung cancer, etc. In some embodiments, these compounds may be used in combination with or as an adjuvant/sensitizer for any chemotherapy regimen. Such regimens may include the use of other anti-cancer compounds, e.g., taxol, Herceptin, Gleevac, etc. The additions may be made simultaneously or sequentially and, if the latter, in any order.

In some aspects, the compounds or compositions are used for non-oncology applications, e.g., treating inflammation, infectious disease, autoimmune disease, and ischemia.

The individual steps prescribed for various methods of the invention do not preclude the utilization of other, unspecified steps, and those of ordinary skill in the art will appreciate that additional steps and compounds may also be usefully incorporated in the spirit of the invention. Thus, combinational applications and therapies are also envisioned in some method embodiments of the invention.

It is understood that any of the above described embodiments of the invention can be combined where practical.

Other advantages, aspects, and embodiments of the invention will be apparent from the figures, the detailed description, and the claims to follow.

DETAILED DESCRIPTION OF THE INVENTION

Definitions

Figure 1:
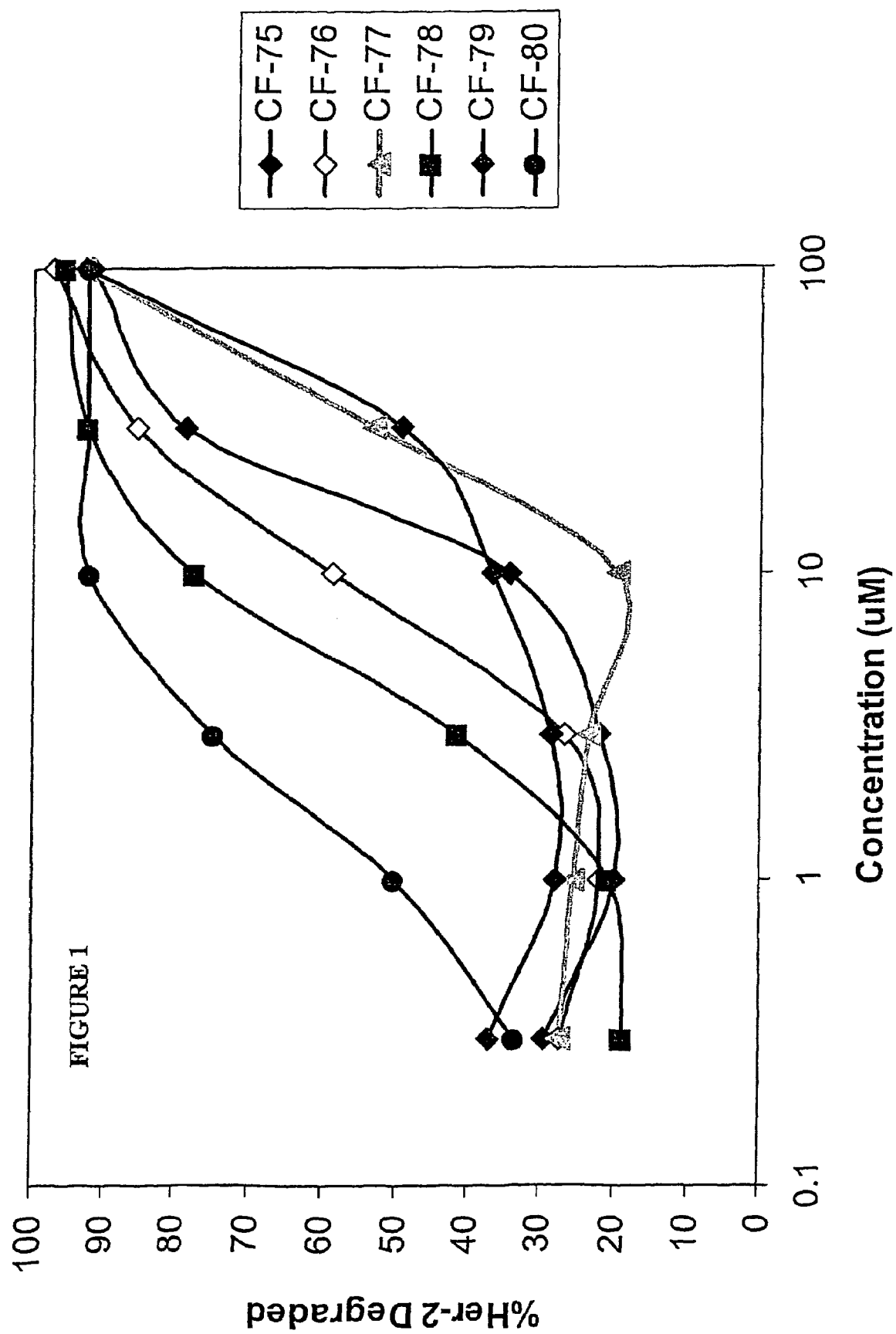
FIG. 1 shows Applicants' IC50 determinations for various commercially available zearalanol compounds as measured using Her-2 degradation studies.

A "pharmaceutically acceptable salt" may be prepared for any compound of the invention having a functionality capable of forming a salt, for example an acid or base functionality. Pharmaceutically acceptable salts may be derived from organic or inorganic acids and bases.

Compounds of the invention that contain one or more basic functional groups, e.g., amino or alkylamino, are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of suitable acids include hydrochloric, hydrobromic, sulfuric, nitric, perchloric, fumaric, maleic, phosphoric, glycolic, gluconic, lactic, salicylic, succinic, toluene-p-sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. See, e.g., Berge et al. "Pharmaceutical Salts", J. Pharm. Sci. 66:1-19 (1977).

Compounds of the present invention that contain one or more acidic functional groups are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. See, for example, Berge et al., supra.

A "pharmaceutically effective amount" or an "effective amount" means an amount which provides a therapeutic and/or prophylactic effect though inhibition of an HSP90. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate and half-life and maximum tolerated dose (MTD) have yet to be determined but one of ordinary skill in the art can determine these using standard procedures.

In some embodiments, the preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

The HSP90 "$IC_{50}$" is preferably greater for normal cells than for cells exhibiting a proliferative disorder, e.g., breast cancer cells.

By a "standard" is meant a positive or negative control. A negative control in the context of HER-2 expression levels is, e.g., a sample possessing an amount of HER-2 protein that correlates with a normal cell. A negative control may also include a sample that contains no HER-2 protein. By contrast, a positive control does contain HER-2 protein, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cells with high as opposed to relatively low or normal Her-2 levels, as in certain breast cancers.

The term "synthetic," as described previously, contrasts with a natural compound that is merely isolated and/or purified from nature.

The term "alkyl," alone or in combination, refers to an optionally substituted straight-chain or branched-chain alkyl radical having from 1 to about 12 carbon atoms. The term "lower alkyl" includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain alkyl radicals having one or more carbon-carbon double bonds and having from 2 to about 6 carbon atoms as well as those having from 2 to about 4 carbon atoms. Examples of alkenyl radicals include ethenyl, propenyl, 1,4-butadienyl and the like.

The term "alkynyl," alone or in combination, refers to an optionally substituted straight-chain or branched-chain hydrocarbon radical having one or more carbon-carbon triple-bonds and having from 2 to about 12 carbon atoms. The term also includes substituted straight-chain or branched-chain alkyl radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The term "heteroalkyl" refers to alkyl groups, as described above, in which one or more skeletal atoms are oxygen, nitrogen, sulfur or combinations thereof. The term heteroalkyl also includes alkyl groups in which one 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof.

The term "alkoxy," alone or in combination, refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as below. Examples of aryloxy radicals include phenoxy, benzyloxy and the like.

The term "alkylthio," alone or in combination, refers to an alkyl thio radical wherein the term alkyl is defined as above.

The term "arylthio," alone or in combination, refers to an aryl thio radical wherein the term aryl is defined as below.

The term "oxo" refers to =O.

The term "aryl," alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen and sulfur. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "heteroarylalkyl" refers to a C1-C4 alkyl group containing a heteroaryl group, each of which may be optionally substituted.

The term "acyloxy" refers to the ester group —OC(O)—R, where R is hydrogen, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

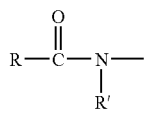

where R and R' each independently is selected from the group of hydrogen, alkyl, aryl and arylalkyl, wherein the alkyl, aryl and arylalkyl groups may be optionally substituted.

The term "cycloalkyl", alone or in combination, refers to a monocyclic, bicyclic or tricyclic alkyl radical wherein each cyclic moiety has from 3 to about 8 carbon atoms. Examples of cycloalkyl radicals include cyclopropyl, cyclobutyl, cyclopentyl, cyclohexyl and the like.

The term "arylalkyl," alone or in combination, refers to an alkyl radical as defined above in which one hydrogen atom is replaced by an aryl radical as defined above, such as, for example, benzyl, 2-phenylethyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, or combinations thereof.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

"Optionally substituted" groups may be substituted or unsubstituted. The substituents of an "optionally substituted" group may include, without limitation, one or more substituents independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, oximes, carboxyesters, carboxamido, acyloxy, hydrogen, F, Cl, Br, I, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, $OR^{17}$, $SR^{17}$ and $NR^{18}R^{19}$. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). $R^{17}$ is selected from the group of hydrogen, F, Cl, Br, I, CN, C1-C8 alkyl, C1-C8 heteroalkyl, C1-C8 haloalkyl, C2-C8 alkenyl, C2-C8 heteroalkenyl, C2-C8 haloalkenyl, C2-C8 alkynyl, C2-C8 heteroalkynyl, C2-C8 haloalkynyl, aryl, and heteroaryl wherein said alkyl, heteroalkyl, haloalkyl, alkenyl, heteroalkenyl, haloalkenyl, alkynyl, heteroalkynyl, haloalkynyl, aryl and heteroaryl groups are optionally substituted with F, Cl, Br, I, $NO_2$, CN, $OR^{18}$, $SR^{18}$, $NR^{18}R^{19}$, C1-C6 alkyl, C1-C6 haloalkyl, C2-C6 alkynyl, C2-C6 alkenyl, or allyl. $R^{18}$ and $R^{19}$ are each independently selected from the group of hydrogen, a $C_1$-$C_6$ alkyl, a $C_1$-$C_6$ heteroalkyl, and $C_1$-$C_6$ haloalkyl.

The term "halogen" or "halo" includes F, Cl, Br and I.

Ring-closing-metathesis ("RCM") is a new and emerging tool for synthetic organic chemists. The method is based on a chemical transformation which transposes the substituents of carbon-carbon double bonds.

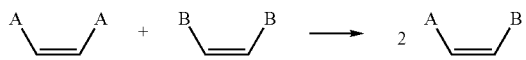

Mechanistic studies have shown that the reaction proceeds by stepwise cleavage and rejoining of carbon-carbon double bonds rather than scission and reformation of olefin substituent bonds. In one aspect of ring-closure metathesis, the two "outer" ends of a ring precursor become a molecule of ethylene ($CH_2=CH_2$) while the two "inner" ends of the olefin join:

The ring-closed product contains two fewer carbons than the precursor; the remainder forming ethylene. RCM reactions are largely driven by entropic forces, i.e., making two molecules from one is thermodynamically downhill or "favorable." The RCM reaction is typically catalyzed by low-valent ruthenium catalysts. While RCM catalysts are still evolving, recent generations have been shown to be quite tolerant of an extremely broad range of functional groups.

Examples of the preferred compounds include, but are not limited to those described in Table 1, these include salts and prodrugs thereof:

TABLE 1

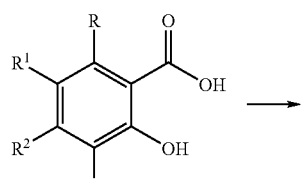

| S. No | Example # | $R_1$ | $R_2, R_3$ | $n_1, n_2$ | a, b | Y, Z |
|---|---|---|---|---|---|---|
| 1 | 1 | H | H, H | 2, 2 | $OCH_2$ | CH(OH)CH(OH) |
| 2 | 2.1 | Ac | H, H | 2, 2 | $OCH_2$ | CH=CH |
| 3 | 2.2 | Ac | Ac, H | 2, 2 | $OCH_2$ | CH=CH |
| 4 | 3.1 | H | H, H | 2, 2 | $OCH_2$ | $CH_2$—C=O |
| 5 | 3.2 | H | H, H | 2, 2 | $OCH_2$ | O=C—$CH_2$ |
| 6 | 4 | H | H, H | 1, 1 | $OCH_2$ | CH(OH)CH(OH) |
| 7 | 5.1 | Ac | H, H | 1, 1 | $OCH_2$ | (Z)CH=CH |
| 8 | 5.2 | Ac | H, H | 1, 1 | $OCH_2$ | (E)CH=CH |
| 9 | 6 | Me | H, Me | 1, 1 | CH=CH | $CH_2$C=O |
| 10 | 7 | H | H, Me | 1, 1 | CH=CH | $CH_2$C=O |

Synthesis of the Compounds of the Invention

The following synthetic scheme is generally applicable to the compounds of formula I:

Synthesis of compounds of formula I of the present invention typically includes some or all of the following steps: The persubstituted o-hydroxy benzoic acid of formula 3 can react with alcohols, amines or thiols under Mitsunobu conditions (see Hughes, Org. React., 42, 335 (1992)) or any carbon electrophile/nucleophile coupling reaction after Stille coupling with vinyltributyltin (see Stille et al., J. Am. Chem. Soc. 109, 5478 (1987)) or any suitable carbon-carbon bond-forming reaction to give the corresponding esters, amides and thioesters of formula 2. This latter can cyclize by ring closure methathesis to give the compounds I (see Furstner et al., Tetrahedron 55, 8215-8230 (1999)).

The following synthetic scheme is generally applicable to the compounds of formula II:

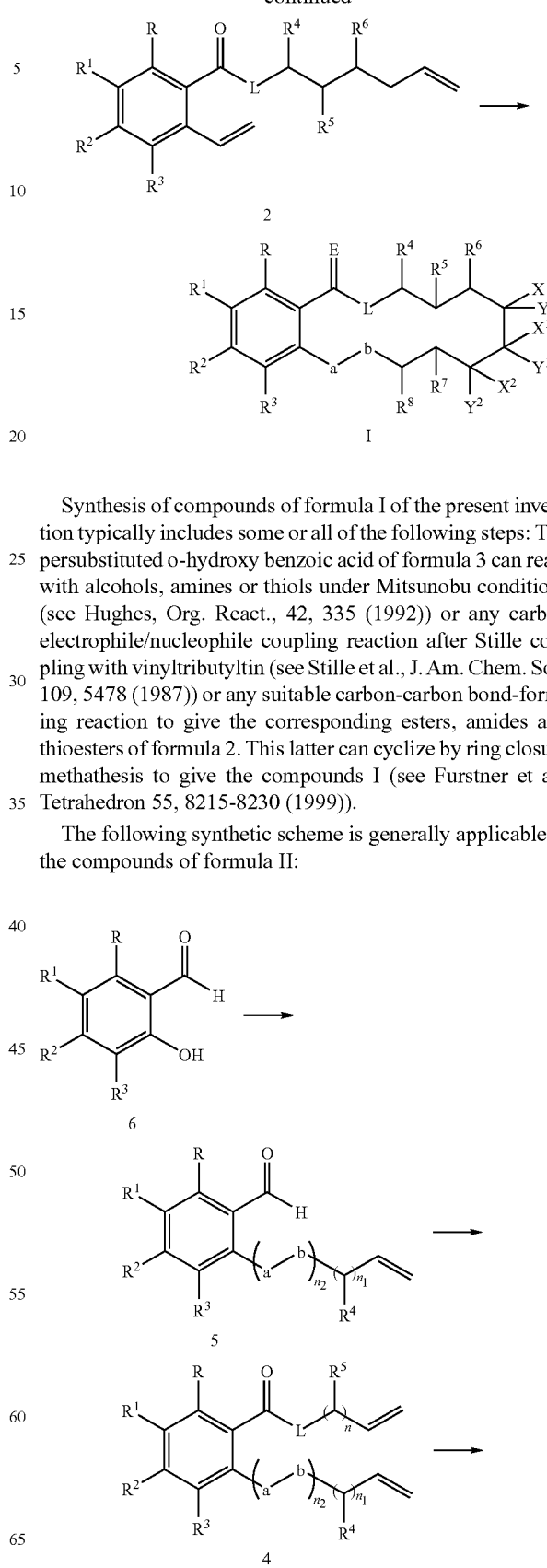

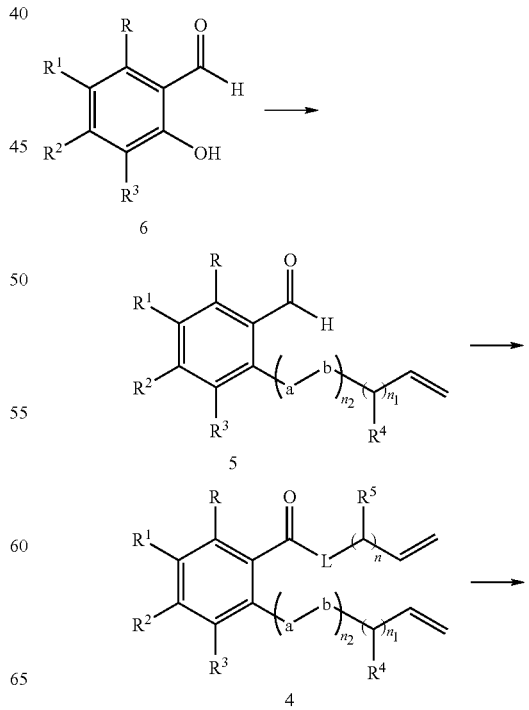

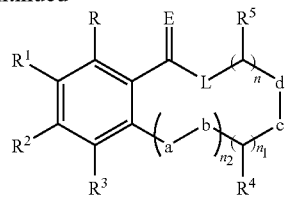

II

Synthesis of compounds of formula II of the present invention typically includes some or all of the following steps: Treatment of the o-hydroxy benzaldehyde of formula 6 under basic conditions in the presence of alkenyl bromide in DMF leads to an alkene of formula 5, which can then undergo addition of a vinyl Grignard, e.g., an alkenyl magnesium bromide in TBF, followed by oxidation with pyridinium chlorochromate (C5H5NH(+)CrO3Cl(−)) ("PCC") to give the diene of formula 4 which cyclizes into the compounds II by ring closure methathesis (see Furstner et al., Tetrahedron 55, 8215-8230 (1999)).

Alternatively, the compounds of formula 13 can undergo bis alkylation in the presence of alkenyl halide under basic conditions to afford the corresponding o-alkenyloxy-alkenyl ester 12. Compound 12 can be cyclized by ring closure metathesis to give the compound 11 which can undergo dihydroxylation (see Bates et al. J. Org. Chem., 51, 2637 (1986)) or Wacker oxidation (see Wayner et al., J. Org. Chem., 55, 2924 (1990)) to give the compounds II.

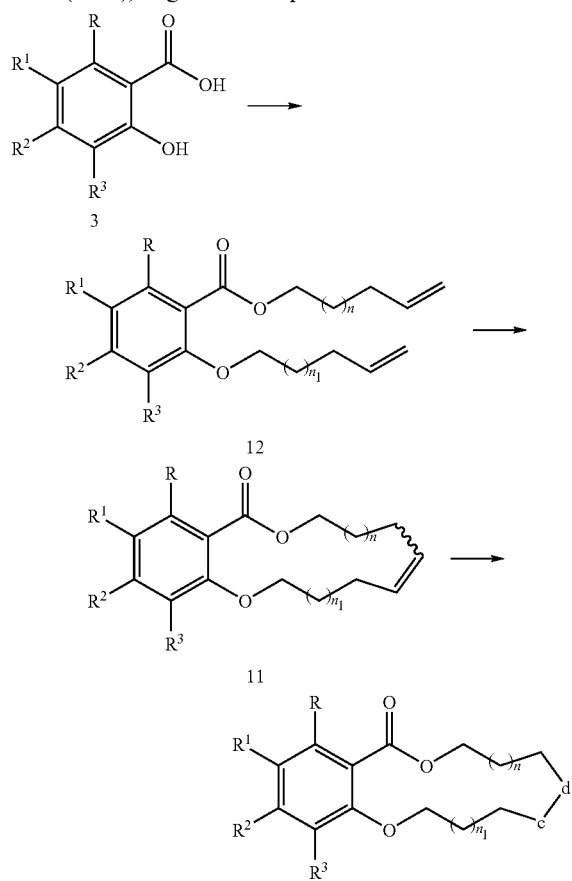

The following synthetic scheme is generally applicable to the compounds of formula III:

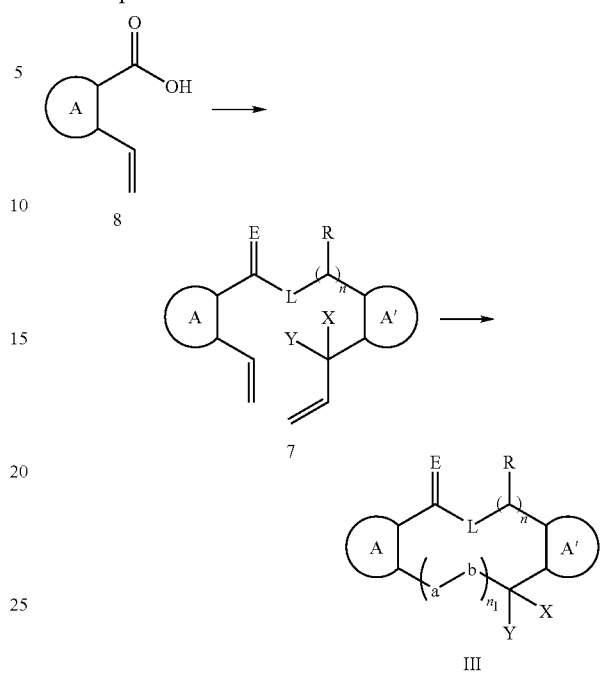

Synthesis of compounds III of the present invention typically includes some or all of the following steps: O-vinyl-carboxylic acid of formula 8 can react with alcohols, amines or thiols under Mitsunobu conditions (see Hughes, Org. React., 42, 335 (1992)) to give the bicyclic intermediate of formula 7 which cyclizes to give the compound III by ring closure methathesis (see Furstner et al., Tetrahedron 55, 8215-8230 (1999)).

The following synthetic scheme is generally applicable to the compounds of formula IV:

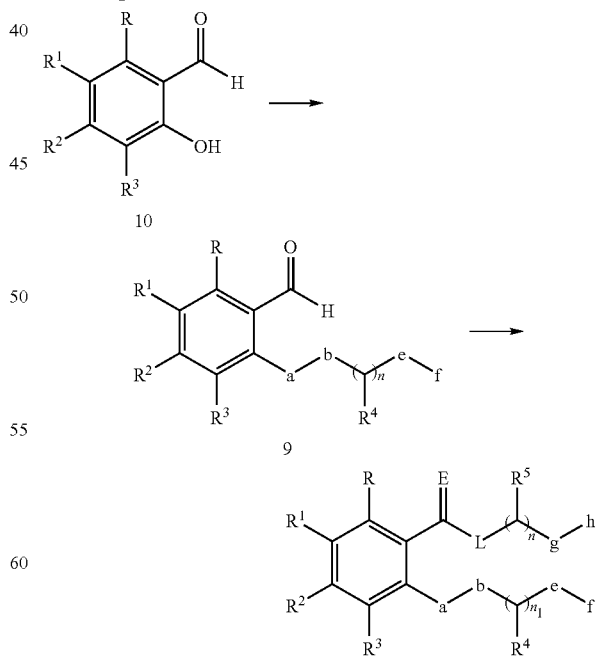

Synthesis of compounds IV of the present invention typically includes some or all of the following steps: Treatment of the o-hydroxy benzaldehyde of formula 10 under basic conditions in the presence of substituted alkyl bromide in DMF leads to the aldehyde of formula 9 which, after oxidation with $NaClO_2$, can react with alcohols, amines or thiols under Mitsunobu conditions to give the compound IV (see Hughes, Org. React., 42, 335 (1992)).

The foregoing reaction schemes may be used to construct compounds of the invention, which may then be tested for HSP90 inhibition activity.

Pharmaceutical Compositions, Dosaging, and Modes of Administration

Those of ordinary skill in the art are familiar with formulation and administration techniques that can be employed in use of the invention, e.g., as discussed in Goodman and Gilman's, The Pharmacological Basis of Therapeutics, current edition; Pergamon Press; and Remington's Pharmaceutical Sciences (current edition.) Mack Publishing Co., Easton, Pa.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intraventous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g, out of a porous, non-porous, or gelatinous material, including membranes, such as sialastic membranes, or fibers. The administration can also be by direct injection at the site (or former site) of a tumor or neoplastic or pre-neoplastic tissue.

Still further, the therapeutic or pharmaceutical composition can be delivered in a vesicle, e.g., a liposome (see, for example, Langer, 1990, Science, 249:1527-1533; Treat et al., 1989, Liposomes in the Therapy of Infectious Disease and Cancer, Lopez-Bernstein and Fidler (eds.), Liss, N.Y., pp. 353-365).

The pharmaceutical compositions used in the methods of the present invention can be delivered in a controlled release system. In one embodiment, a pump may be used (see, Sefton, 1987, CRC Crit. Ref. Biomed. Eng. 14:201; Buchwald et al., 1980, Surgery, 88:507; Saudek et al., 1989, N. Engl. J. Med., 321:574). Additionally, a controlled release system can be placed in proximity of the therapeutic target. (see, Goodson, 1984, Medical Applications of Controlled Release, Vol. 2, pp. 115-138).

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, or cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The HSP90 inhibitors used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an HSP90 inhibitor can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods and compounds of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of antineoplastic agents, which can be used in combination with the methods of the present invention include, in general, alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the epothilones, discodermolide, the pteridine family of drugs, diynenes and the podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a HSP90 inhibitor used in the methods of the present invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer, for example, breast cancer. Administration typically occurs in an amount of between about 0.01 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 1000 mg of compound, and preferably includes, e.g., from about 1 mg to about 1000 mg. The quantity of active compound in a unit dose of preparation may be varied or adjusted from about 0.1 mg to 1000 mg, preferably from about 1 mg to 300 mg, more preferably 10 mg to 200 mg, according to the particular application. The amount administered will vary depending on the particular IC50 value of the compound used and the judgment of the attending clinician taking into consideration factors such as health, weight, and age.

Preferably, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the HSP90 inhibitors used in the methods of the present invention and if applicable other chemotherapeutic agents and/or radiation therapy will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the HSP90 inhibitor and the chemotherapeutic agent do not have to be administered in the same pharmaceutical composition, and may, because of different physical and chemical characteristics, have to be administered by different routes. For example, the HSP90 inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of HSP90 inhibitor, and chemotherapeutic agent and/or radiation will depend upon the diagnosis of the attending physicians and their judgment of the condition of the patient and the appropriate treatment protocol.

The HSP90 inhibitor, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the HSP90 inhibitor.

If the HSP90 inhibitor and the chemotherapeutic agent and/or radiation are not administered simultaneously or essentially simultaneously, then the initial order of administration of the HSP90 inhibitor, and the chemotherapeutic agent and/or radiation, may not be important. Thus, the HSP90 inhibitor may be administered first followed by the administration of the chemotherapeutic agent and/or radiation; or the chemotherapeutic agent and/or radiation may be administered first followed by the administration of the HSP90 inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the HSP90 inhibitor followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent—i.e., HSP90 inhibitor, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The following Examples are offered by way of illustration only, and components and steps included therein are not intended to be limiting of the invention.

Assays to Determine HSP90 Binding and Downstream Effect

A variety of in vitro and in vivo assays are available to test the effect of the compounds of the invention on HSP90. HSP90 competitive binding assays and functional assays can be performed as known in the art substituting in the compounds of the invention. Chiosis et al., Chemistry & Biology 8:289-299 (2001), describe some of the known ways in which this can be done. For example, competition binding assays using, e.g., geldanamycin or 17-AAG as a competitive binding inhibitor of HSP90 can be used to determine relative HSP90 affinity of the compounds of the invention by immobilizing the compound of interest or other competitive inhibitor on a gel or solid matrix, preincubating HSP90 with the other inhibitor, passing the preincubated mix over the gel or matrix, and then measuring the amount of HSP90 that sticks or does not stick to the gel or matrix.

Downstream effects can also be evaluated based on the known effect of HSP90 inhibition on function and stability of various steroid receptors and signaling proteins including, e.g., Raf1 and Her2. HSP90 inhibitors induce dose-dependent degradation of these molecules, which can be measured using standard techniques. Inhibition of HSP90 also results in up-regulation of HSP90 and related chaperone proteins that can similarly be measured. Antiproliferative activity on various cancer cell lines can also be measured, as can morphological and functional differentiation related to HSP90 inhibition. For example, the Many different types of methods are known in the art for determining protein concentrations and measuring or predicting the level of proteins within cells and in fluid samples.

Indirect techniques include nucleic acid hybridization and amplification using, e.g., polymerase chain reaction (PCR). These techniques are known to the person of skill and are discussed, e.g., in Sambrook, Fritsch & Maniatis, Molecular Cloning: A Laboratory Manual, Second Edition (1989) Cold Spring Harbor Laboratory Press, Cold Spring Harbor, N.Y., Ausubel, et al., Current Protocols in Molecular Biology, John Wiley & Sons, NY, 1994, and, as specifically applied to the quantification, detection, and relative activity of Her-2/neu in patient samples, e.g., in U.S. Pat. Nos. 4,699,877, 4,918,162, 4,968,603, and 5,846,749. A brief discussion of two generic techniques that can be used follows.

The determination of whether cells overexpress or contain elevated levels of HER-2 can be determined using well known antibody techniques such as immunoblotting, radio-immunoassays, western blotting, immunoprecipitation, enzyme-linked immunosorbent assays (ELISA), and derivative techniques that make use of antibodies directed against HER-2. As an example, HER-2 expression in breast cancer cells can be determined with the use of an immunohistochemical assay, such as the Dako Hercep™ test (Dako Corp., Carpinteria, Calif.). The Hercep™ test is an antibody staining assay designed to detect HER-2 overexpression in tumor tissue specimens. This particular assay grades HER-2 expression into four levels: 0, 1, 2, and 3, with level 3 representing the highest level of HER-2 expression. Accurate quantitation can be enhanced by employing an Automated Cellular Imaging System (ACIS) as described, e.g., by Press, M, et al, 2000, Modern Pathology 13:225A.

Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

HER-2 overexpression can also be determined at the nucleic acid level since there is a reported high correlation between overexpression of the HER-2 protein and amplification of the gene that codes for it. One way to test this is by using RT-PCR. The genomic and cDNA sequences for HER-2 are known. Specific DNA primers can be generated using standard, well-known techniques, and can then be used to amplify template already present in the cell. An example of this is described in Kurokawa, H et al, Cancer Res. 60: 5887-5894 (2000), (which describes a forward primer having sequence 5'-TCTGGACGTGCCAGTGTGAA-3' (SEQ ID NO. 1) and a reverse primer having sequence 5'-TGCTCCCT-GAGGACACATCA-3' (SEQ ID NO. 2)). PCR can be standardized such that quantitative differences are observed as between normal and abnormal cells, e.g., cancerous and non-cancerous cells. Well known methods employing, e.g., densitometry, can be used to quantitate and/or compare nucleic acid levels amplified using PCR.

Similarly, fluorescent in situ hybridization (FISH) assays and other assays can be used, e.g., Northern and/or Southern blotting. These rely on nucleic acid hybridization between the HER-2 gene or mRNA and a corresponding nucleic acid probe that can be designed in the same or a similar way as for PCR primers, above. See, e.g., Mitchell M S, and Press M F., 1999, Semin. Oncol., Suppl. 12:108-16. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, Cancer Res. 60: 5887-5894 (2000) (describing a nucleic acid probe having sequence 5'-FAM-CA-GAAGGCCAAGTCCGCAGAAGCC-TAMRA-p-3' (SEQ ID NO. 3)). ACIS-based approaches as described above can be employed to make the assay more quantitative (de la Torre-Bueno, J, et al, 2000, Modern Pathology 13:221A).

Immuno and nucleic acid detection can also be directed against proteins other than HSP90 and Her-2, which proteins are nevertheless affected in response to HSP90 inhibition.

The following examples are offered by way of illustration only and are not intended to be limiting of the full scope and spirit of the invention.

EXAMPLES

The chemical reagents recited below are all available commercially and/or their preparation known to one of ordinary skill in the art.

Example 1

Preparation of 1,10,11-trihydroxy-3-methoxy-6,7,8,9,12,13,14,15-octahydro-5,16-dioxa-benzocyclopentadecen-17-one, 1

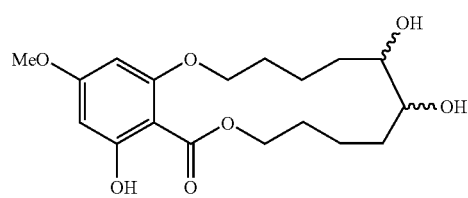

Compound 1 was synthesized in 4 steps:

Step A: A mixture of 4,6-dimethoxy-2-hydroxy benzoic (0.5 g, 2.57 mmol), 6-Bromo-1-hexene (0.86 ml, 6.4 mmol) and potassium carbonate (0.88 g, 6.4 mmol) in dimethyl formamide (10 ml) was heated at 50° C. for 12 h whereby it was poured into water (100 ml). Extraction with EtOAc and chromatography gave the 2-hex-5-enyloxy-4,6-dimethoxy-benzoic acid hex-5-enyl ester (545 mg).

Step B: To a solution of bis(tricyclohexylphosphine)benzylidine ruthenium IV dichloride (39 mg, 0.045 mmol) in dichloromethane (150 ml) at reflux was transferred a solution of 2-hex-5-enyloxy-4,6-dimethoxy-benzoic acid hex-5-enyl ester (430 mg, 1.18 mmol) in dichloromethane (100 ml). After 5 hours at reflux, the solvent was removed and chromatography gave the 1,3-dimethoxy-6,7,8,9,12,13,14,15-octahydro-5,16-dioxa-benzocyclopentadecen-17-one (370 mg).

Step C: A solution of 1,3-dimethoxy-6,7,8,9,12,13,14,15-octahydro-5,16-dioxa-benzocyclopentadecen-17-one (321 mg, 0.96 mmol) and sodium thioethoxide (97 mg, 1.15 mmol) in dimethyl formamide was heated at 140° C. for 4 h whereby it was poured into water (100 ml). Extraction and chromatography gave 1-hydroxy-3-methoxy-6,7,8,9,12,13,14,15-octahydro-5,16-dioxa-benzocyclopentadecen-17-one (117 mg).

Step D: A solution of 1-hydroxy-3-methoxy-6,7,8,9,12,13,14,15-octahydro-5,16-dioxa-benzocyclopentadecen-17-one (12 mg, 0.037 mmol) in acetone (1 ml) was treated with $OsO_4$(2.5% in t-BuOH, 20 μl, 0.0015 mmol) and NMO (7.5 mg, 0.055 mmol). After 2 h, the solvent was removed under reduce pressure and the residue was dissolved in EtOAc (10 ml) and washed with $Na_2S_2O_3$ 0.1M (1 ml), dried over $Na_2SO_4$ and purified by preparative thin layer chromatography (500 μM) to give the title compound 1 as a 1/1 mixture diastereomers (12 mg). Rf=0.10 in 50:50 EtOAc:Hexane. $^1$H NMR $CDCl_3$ δ 1.48-1.90 (m, 10H), 1.96-2.00 (m, 2H), 2.25 (br s, 1H), 3.59 (br s, 1H), 3.80 (br s, 4H), 3.84-4.06 (m, 2H), 4.22-4.25 (m, 0.5H), 4.29-4.34 (m, 0.5H), 4.48-4.51 (m, 0.5H), 4.58-4.62 (m, 0.5H), 5.93 (d, 0.5H), 5.935 (d, 0.5H), 6.09 (d, 0.5H), 6.10 (d, 0.5H), 12.23 (s, 0.5H), 12.25 (s, 0.5H).

Example 2

Preparation of 1-acetoxy-3-methoxy-6,7,8,9,12,13,14,15-octahydro-5,16-dioxa-benzocyclopentadecen-17-one (2.1) and 1-acetoxy-3-methoxy-4-acetyl-6,7,8,9,12,13,14,15-octahydro-5,16-dioxa-benzocyclopentadecen-17-one (2.2)

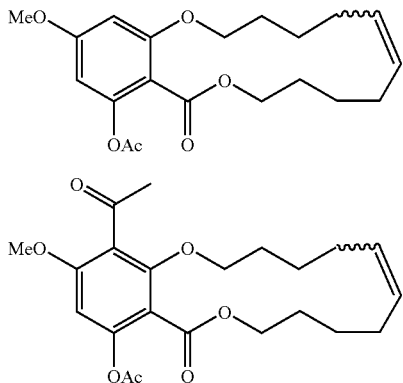

A solution of 1,3-dimethoxy-6,7,8,9,12,13,14,15-octahydro-5,16-dioxa-benzocyclopentadecen-17-one (15 mg, 0.047 mmol) and FeCl₃ (1.5 mg, 0.0094 mmol) in Ac₂O (1 ml) was heated at 100° C. for 19 h. After this time, the reaction mixture was concentrated under reduce pressure and the residue was dissolved in EtOAc (8 ml), washed with sat. NaHCO₃ (1 ml) and dried over Na₂SO₄. After concentration, the residue was purified by preparative thin layer chromatography (500 μM) to give both the title compounds 2.1 (10 mg) and 2.2 (2 mg).

2.1: Rf=0.50 in 20:80 EtOAc:Hexane. ¹H NMR CDCl₃ δ 1.43-1.50 (m, 2H), 1.51-1.58 (m, 2H), 1.73-1.83 (m, 4H), 2.00-2.10 (m, 4H), 2.25 (s, 3H), 3.78 (s, 3H), 3.92 (t, 1H), 3.97 (t, 1H), 4.21 (t, 1H), 4.31 (t, 1H), 5.27-5.35 (m, 0.5H), 5.40-5.57 (m, 1.5H), 6.23 (d, 0.5H), 6.24 (d, 0.5H), 6.31 (d, 1H).

2.2: Rf=0.25 in 20:80 EtOAc:Hexane. ¹H NMR CDCl₃ δ 1.42-1.50 (m, 2H), 1.52-1.59 (m, 2H), 1.71-1.85 (m, 4H), 2.00-2.13 (m, 4H), 2.20 (s, 3H), 2.45 (s, 3H), 3.88 (s, 3H), 4.00 (t, 1H), 4.04 (t, 1H), 4.21 (t, 1H), 4.30 (t, 1H), 5.28-5.35 (m, 0.5H), 5.41-5.57 (m, 1.5H), 6.32 (d, 1H).

Example 3

Preparation of 1-hydroxy-3-methoxy-6,7,8,9,12,13,14,15-octahydro-11H-5,16-dioxa-benzocyclopentadecene-10,17-dione (3.1) and 1-Hydroxy-3-methoxy-6,7,8,9,12,13,14,15-octahydro-11H-5,16-dioxa-benzocyclopentadecene-11,17-dione (3.2).

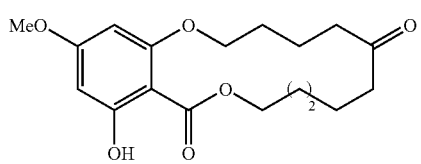

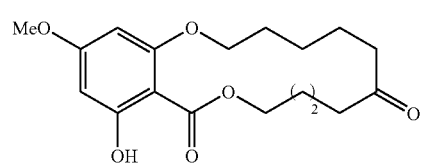

To 1-hydroxy-3-methoxy-6,7,8,9,12,13,14,15-octahydro-5,16-dioxa-benzocyclopentadecen-17-one (3.5 mg, 0.011 mmol) was added a premixed solution of palladium acetate (0.12 mg, 0.0055 mmol) and benzoquinone (1.1 mg, 0.011 mmol) in 7/1 CH₃CN/H₂O mixture (0.5 ml). After 12 h at rt, the reaction mixture was concentrated under reduce pressure and the residue was dissolved in EtOAc (5 ml), washed with Na₂S₂O₃ 0.1M (1 ml) and dried over Na₂SO₄. After concentration, the residue was purified by preparative thin layer chromatography (500 μM) to give the title compounds 3.1 (1.8 mg) and 3.2 (0.8 mg).

3.1: Rf=0.29 in 20:80 EtOAc:Hexane. ¹H NMR CDCl₃ δ 1.48-1.56 (m, 2H), 1.77-1.85 (m, 8H), 2.48-2.51 (m, 4H), 3.80 (s, 3H), 3.96 (t, 2H), 4.32 (t, 2H), 5.925 (d, 1H), 6.10 (d, 1H), 12.36 (s, 1H).

3.2: Rf=0.24 in 20:80 EtOAc:Hexane. ¹H NMR CDCl₃ δ 1.46-1.52 (m, 2H), 1.75-1.86 (m, 8H), 2.50 (t, 4H), 3.80 (s, 3H), 3.96 (t, 2H), 4.34 (t, 2H), 5.93 (d, 1H), 6.10 (d, 1H), 12.36 (s, 1H).

Example 4

Preparation of 1,9,10-Trihydroxy-3-methoxy-6,7,8,9,10,11,12,13-octahydro-5,14-dioxa-benzocyclotridecen-15-one

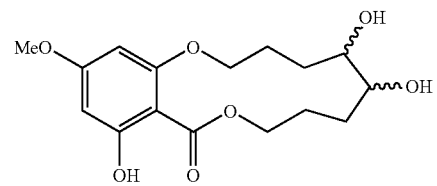

Compound 4 was synthesized in 4 steps:

Step A: A mixture of 4,6-dimethoxy-2-hydroxybenzoic (0.3 g, 1.51 mmol), 5-Bromo-1-pentene (0.43 ml, 3.6 mmol) and potassium carbonate (0.5 g, 3.6 mmol) in dimethyl formamide (8 ml) was heated at 50° C. for 12 h whereby it was poured into water (80 ml). Extraction with EtOAc and chromatography gave the 2,4-dimethoxy-6-pent-4-enyloxy-benzoic acid pent-4-enyl ester (268 mg).

Step B: To a solution of bis(tricyclohexylphosphine)benzylidine ruthenium IV dichloride (39 mg, 0.045 mmol) in dichloromethane (100 ml) at reflux was transferred a solution of 2,4-dimethoxy-6-pent-4-enyloxy-benzoic acid pent-4-enyl ester (255 mg, 0.76 mmol) in dichloromethane (70 ml). After 5 hours at reflux, the solvent was removed and chromatography gave the 1,3-dimethoxy-6,7,8,11,12,13-hexahydro-5,14-dioxa-benzocyclotridecen-15-one (225 mg).

Step C: A solution of 1,3-dimethoxy-6,7,8,11,12,13-hexahydro-5,14-dioxa-benzocyclotridecen-15-one (95 mg, 0.30 mmol) and sodium thioethoxide (31 mg, 0.37 mmol) in dimethyl formamide was heated at 140° C. for 4 h whereby it was poored into water (100 ml). Extraction and chromatography gave 1-hydroxy-3-methoxy-6,7,8,11,12,13-hexahydro-5,14-dioxa-benzocyclotridecen-15-one (20 mg).

Step D: A solution of 1-hydroxy-3-methoxy-6,7,8,11,12,13-hexahydro-5,14-dioxa-benzocyclotridecen-15-one (12 mg, 0.041 mmol) in acetone (1 ml) was treated with $OsO_4$ (2.5% in t-BuOH, 22 μl, 0.0015 mmol) and NMO (8.3 mg, 0.061 mmol). After 2 h, the solvent was removed under reduce pressure and the residue was dissolved in EtOAc (10 ml) and washed with $Na_2S_2O_3$ 0.1M (1 ml), dried over $Na_2SO_4$ and purified by preparative thin layer chromatography (500 μM) to give the title compound 4 as a 1/1 mixture diastereomers (12 mg).

4: Rf=0.10 in 50:50 EtOAc:Hexane. $^1$H NMR $CDCl_3$ δ 1.66-1.80 (m, 4H), 1.82-1.96 (m, 4H), 3.78 (s, 3H), 3.83-3.89 (m, 2.5H), 3.92-3.96 (m, 0.5H), 3.96-4.02 (m, 1H), 4.08-4.12 (m, 0.5H), 4.17-4.22 (m, 0.5H), 4.49-4.55 (m, 0.5H), 4.60-4.65 (m, 0.5H), 5.90 (d, 0.5H), 5.905 (d, 0.5H), 6.07 (d, 1H), 12.01 (s, 1H).

Example 5

Preparation of (9Z)-1-acetoxy-3-methoxy-6,7,8,11,12,13-hexahydro-5,14-dioxa-benzocyclotridecen-15-one (5.1) and (9E)-1-acetoxy-3-methoxy-6,7,8,11,12,13-hexahydro-5,14-dioxa-benzocyclotridecen-15-one (5.2)

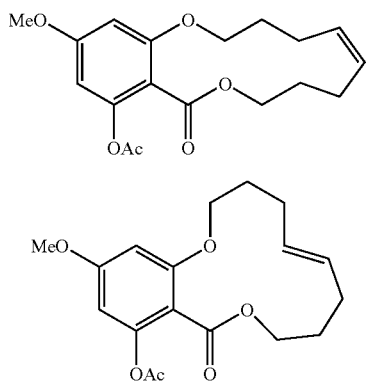

To a solution of 1-hydroxy-3-methoxy-6,7,8,11,12,13-hexahydro-5,14-dioxa-benzocyclotridecen-15-one (2.4 mg, 0.011 mmol) in $CH_2Cl_2$ (2 ml) was added EtN(i-Pr)$_2$ (19 μl, 0.11 mmol) and $Ac_2O$ (5 μl, 0.057 mmol) at 0° C. After 5 h at rt, the reaction mixture was diluted with EtOAc (10 ml), washed with 2N HCl (1 ml), with sat. $NaHCO_3$ (1 ml) and dried over $Na_2SO_4$. After concentration, the residue was purified by preparative thin layer chromatography to give the title compounds 5.1 (1.2 mg) and 5.2 (1.3 mg).

5.1: Rf=0.33 in 20:80 EtOAc:Hexane. $^1$H NMR $CDCl_3$ δ 1.74-1.86 (m, 4H), 2.22-2.35 (m, 4H), 2.27 (s, 3H), 3.80 (s, 3H), 3.95 (t, 2H), 4.30 (t, 2H), 5.47-5.57 (m, 2H), 6.265 (d, 1H), 6.33 (d, 1H).

5.2: Rf=0.30 in 20:80 EtOAc:Hexane. $^1$H NMR $CDCl_3$ δ 1.84-1.91 (m, 4H), 2.19-2.23 (m, 4H), 2.25 (s, 3H), 3.79 (s, 3H), 4.00 (t, 2H), 4.27 (t, 2H), 5.43-5.55 (m, 2H), 6.24 (d, 1H), 6.31 (d, 1H).

Example 6

Preparation of 2,4-dimethoxy-7-methyl-8,9,12,13-tetrahydro-7H,11H-6-oxa-benzocyclotridecene-5,10-dione

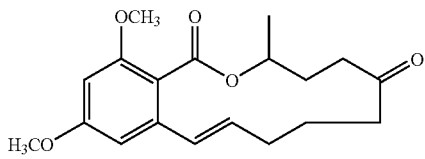

Compound 6 was synthesized in 6 steps:

Step A: To a solution of 5-methyl-dihydro-furan-2-one (0.2 mL, 2.1 mmol) in dichloromethane (10 mL) was added a mixture of $AlCl_3$ (3.1 mL, 6.2 mmol) and methoxylamine hydrochloride (0.6 g, 6.2 mmol) in dichloromethane (20 mL). After 1.5 hours, the reaction was cooled to 0° C. and a saturated sodium bicarbonate solution (10 mL) was added slowly. Extraction and concentration afforded 4-hydroxy-pentanoic acid methoxy-methyl-amide as a clear oil (184 mg).

Step B: A solution of 4-hydroxy-pentanoic acid methoxy-methyl-amide (0.12 g, 0.74 mmol) in tetrahydrofuran (1 mL) was cooled to –78° C., after which a solution of hex-1-ene-magnesium bromide (7.0 ml, 1.56 mmol) was added dropwise. After stirring at –78° C. for 2 hours, saturated ammonium chloride (2 mL) was added, and the reaction mixture allowed to warm to room temperature. Extraction and chromatography afforded 2-hydroxy-dec-9-en-5-one as a clear oil (33 mg).

Step C: A solution of 2-hydroxy-4,6-dimethoxy-benzoic acid (0.36 g, 0.18 mmol), 2-hydroxy-dec-9-en-5-one (0.024 g, 0.14 mmol), $PPh_3$ (0.042 g, 0.16 mmol), diethyl azodicarboxylate (25 μL, 0.15 mmol) in diethyl ether (1.5 mL) was stirred at room temperature for 7 hours. Concentration under vacuum and chromatography afforded 2-hydroxy-4,6-dimethoxy-benzoic acid 1-methyl-4-oxo-non-8-enyl ester as a light yellow oil (32 mg).

Step D: To a solution of 2-hydroxy-4,6-dimethoxy benzoic acid 1-methyl-4-oxo-non-8-enyl ester (0.031 g, 0.089 mmol) in pyridine (0.75 mL) and dichloromethane (0.75 mL) at 0° C. was added triflic anhydride (30 μL, 0.18 mmol) dropwise. After 2 hours, the reaction was quenched by the addition of water (2 mL). Extraction and chromatography afforded 2,4-dimethoxy-6-trifluoromethanesulfonyloxy-benzoic acid 1-methyl-4-oxo-non-8-enyl ester as a viscous yellow oil (41 mg).

Step E: A mixture of 2,4-dimethoxy-6-trifluoromethanesulfonyloxy-benzoic acid 1-methyl-4-oxo-non-8-enyl ester (0.041 g, 0.085 mmol), $PdCl_2(PPh_3)_2$ (0.007 g, 0.01 mmol), lithium chloride (0.052 g, 1.2 mmol), and vinyltributyltin (50 μL, 0.17 mmol) in dimethylformamide (2 mL) was stirred at room temperature for 24 hours. After addition of water (10 mL), extraction, and chromatography afforded 2,4-dimethoxy-6-vinyl-benzoic acid 1-methyl-4-oxo-non-8-enyl ester as a clear oil (23 mg).

Step F: 2,4-dimethoxy-6-vinyl-benzoic acid 1-methyl-4-oxo-non-8-enyl ester (0.023 g, 0.06 mmol) was combined with tricyclohexylphosphine[1,3-bis-(2,4,6-trimethylphenyl)-4,5-dihydroimidazol-2-ylidene] [benzylidine]ruthenium (IV) dichloride (0.003 g, 0.003 mmol) in toluene (16 mL). After stirring at 80° C. for 21 hours, the solution was cooled to room temperature and concentrated under vacuum. Chromatography afforded the title compound 6 as a clear oil. (15 mg).

6: Rf=0.31 in 30:70 Acetone:Hexane. $^1$H NMR (CDCl$_3$, 400 MHz) δ 1.35 (d, 3H), 1.78 (m, 2H), 2.0 (m, 2H), 2.29 (m, 3H), 2.4-2.6 (m, 2H), 2.76 (m, 1H), 3.80 (s, 3H), 3.82 (s, 3H), 5.23 (m, 1H), 5.96 (m, 111), 6.25 (d, 1H), 6.35 (d, 1H), 6.46 (d, 1H)

Example 7

Preparation of 4-hydroxy-2-methoxy-7-methyl-8,9,12,13-tetrahydro-7H,11H-6-oxa-benzocyclotridecene-5,10-dione

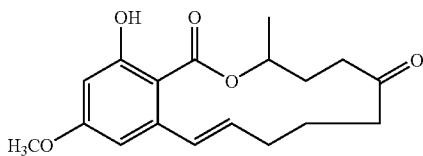

2,4-dimethoxy-7-methyl-8,9,12,13-tetrahydro-7H,11H-6-oxa-benzocyclotridecene-5,10-dione (0.004 g, 0.012 mmol) was added to dichloromethane (1 mL) and cooled to −40° C. A BBr$_3$ solution (0.48 mL, 0.048 mmol) was added to the reaction mixture dropwise, and the reaction stirred for 5 minutes. A small quantity of ice was added to quench the reaction mixture. The solution was allowed to warm to room temperature. Extraction and then purification by preparative thin layer chromatography (500 μM) afforded the title compound 7 as a clear oil.

7: Rf=0.32 in 20% EtOAc/80% Hexanes. $^1$H NMR CDCl$_3$ δ 1.40 (d, 3H), 1.71 (m, 111), 1.96 (m, 1H), 2.2-2.0 (m, 2H), 2.4-2.2 (m, 3H), 2.6-2.5 (m, 3H), 3.81 (s, 3H), 5.13 (m, 1H), 5.71 (m, 1H), 6.39 (m, 2H), 6.80(d, 1H), 12.03 (s, 1H)

Example 8

HER2 Inhibition Assay

MCF-7 cells are seeded in 24 well plates at a density of approximately 30,000 cells/well and allowed to grow for 16 hours in DMEM supplemented with 10% FBS. Drug (a compound as specified in Table I) is then added at a concentration range of 100 μM to 0.01 uM. Cells are incubated for an additional 24. Drug treated cells and untreated control cells are trypsinized, and incubated at room temperature for 15 minutes with anti Her-2 neu Ab conjugated with phycoerythrin (Becton Dickinson, San Jose Calif.; Cat no. 340552) at a concentration of 0.25 ug/ml, or non-specific control IgG1 conjugated with phycoerytirin (Becton Dickinson, San Jose Calif.; Cat no. 340761). Samples were analyzed using a FACS Calibur flow cytometer (Becton Dickinson) equipped with Argon-ion laser that which emits 15 mW of 488 nm light for excitation of the phycoerythrin fluorochrome. 10,000 events were collected per sample. A fluorescence histogram was generated and the mean fluorescence intensity (mfi) of each sample was determined using Cellquest software. The background was defined as the mfi generated from cells incubated with control IgG, and was subtracted from each sample stained with the HER-2/neu Ab. Percent degradation of Her-2 was calculated as follows:

% Her-2 degradation=(mfi HER-2 sample)/(mfi HER-2 untreated cells)×100

Compounds of the following formula (constituents as described in Table I) were acquired from Sigma Aldrich (Milwaukee, Wis.) and evaluated for HSP90 inhibition as manifested by HER2 degradation.

TABLE I

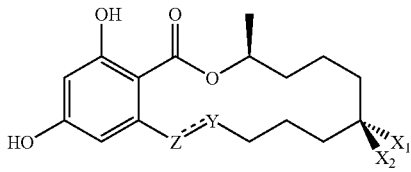

| Compound # | X$_1$, X$_2$ | Y, Z | HER2 IC50 (uM) |
|---|---|---|---|
| 1 (zearalanone) | =O | CH2CH2 | 13 |
| 2 (zearalenone) | =O | CH=CH | 7 |
| 3 (α-zearalanol) | OH, H | CH2CH2 | 30 |
| 4 (β-zearalanol) | H, OH | CH2CH2 | 4 |
| 5 (α-zearalenol) | OH, H | CH=CH | 40 |
| 6 (β-zearalenol) | H, OH | CH=CH | 1 |

It is understood that in compounds 1 and 2 of the preceding Table the double-bonded oxygen constitutes X and Y together.

The following compounds were synthesized and evaluated for Her 2 degradation, with the results reflected in Table 3.

TABLE 3

| Example # | IC50 (μM) |
|---|---|
| 1 | 30 |
| 2.1 | 10 |
| 2.2 | 40 |
| 3.1 | 30 |
| 3.2 | 16 |
| 4 | 12 |
| 5.1 | 13 |
| 5.2 | 15 |
| 6 | 90 |
| 7 | 60 |

The foregoing examples are not limiting and merely illustrative of various aspects and embodiments of the present invention. All documents cited are indicative of the levels of skill in the art to which the invention pertains. The disclosure of each document is incorporated by reference herein to the same extent as if each had been incorporated by reference in its entirety individually, although none of the documents is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

It will be readily apparent to one skilled in the art that varying substitutions and modifications may be made to the invention without departing from the scope and spirit of the invention. Thus, such additional embodiments are within the scope of the invention and the following claims.

The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markash group or other group, and exclusions of individual members as appropriate.

Other embodiments are within the following claims.

We claim:

1. A compound of structure IIa or IIb

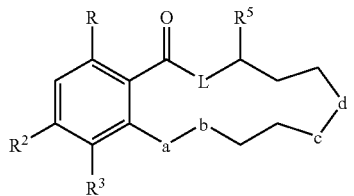

IIa

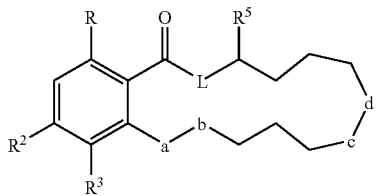

IIb wherein
R and $R^3$ are independently selected from $OR^{10}$, optionally substituted lower alkyl and H;
$R^2$ is —$OCH_3$;
$R^5$ is selected from H, lower alkyl, aryl and perhaloalkyl;
$R^{10}$ is selected from H, lower alkyl, aryl, $C(O)NR^{11}{}_2$, $C(O)OR^{11}$ and $C(O)R^{11}$;
$R^{11}$ is selected from H, optionally substituted alkyl and aryl;
L is O;
"a-b-" is selected from -E-$CH_2$—, -E-C(O)—, and —(O)C-E;
"-c-d-" is selected from CH(OH)—CH(OH), CH═CH, O═C—$CH_2$, and $CH_2$C═O; and
E is O;
wherein the substituents of an optionally substituted group are independently selected from alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, oximes, carboxyesters, carboxamido, acyloxy, F, Cl, Br, I, ON, $NO_2$, $N_3$, $C(O)CH_3$, $CO_2CH_3$, $CO_2H$, $C(O)NH_2$, $OR^{17}$, $SR^{17}$ and $NR^{18}R^{19}$, wherein $R^{17}$ is selected from hydrogen C1-C8 alkyl, C1-C8 heteroalkyl, C1-C8 haloalkyl, C2-C8 alkenyl, C2-C8 heteroalkenyl, C2-C8 haloalkenyl, C2-C8 alkynyl, C2-C8 heteroalkynyl, C2-C8 haloalkynyl, aryl, and heteroaryl wherein said alkyl, heteroalkyl, haloalkyl, alkenyl, heteroalkenyl, haloalkenyl, alkynyl, heteroalkynyl, haloalkynyl, aryl and heteroaryl groups are optionally substituted with F, Cl, Br, I, $NO_2$, CN, $OR^{18}$, $SR^{18}$, $NR^{18}R^{19}$, C1-C6 alkyl, C1-C6 haloalkyl, C2-C6 alkynyl, C2-C6 alkenyl, or allyl, and wherein $R^{18}$ and $R^{19}$ are each independently selected from hydrogen, C1-C6 alkyl, C1-C6 heteroalkyl, and C1-C6 haloalkyl;
or a pharmaceutically acceptable salt thereof.

2. A compound according to claim 1, wherein said compound is represented by the formula:

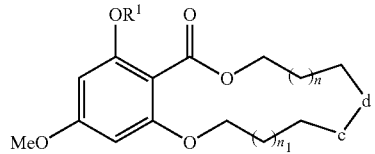

wherein
$R^1$ is selected from H and Ac;
"-c-d-" is selected from CH(OH)—CH(OH) and —CH═CH—; and n and $n_1$ are selected from 1 and 2.

3. A pharmaceutical composition comprising a compound or a pharmaceutically acceptable salt according to claims 1 or 2 and a pharmaceutically acceptable carrier.

4. A compound according to claim 1 of structure IIa wherein
R is —OH;
$R^3$ is H;
$R^5$ is -Me; and
"-c-d-" is —$CH_2$—C(O)—.

5. A compound according to claim 1 of structure IIa wherein
R is —$OCH_3$;
$R^3$ is H;
$R^5$ is -Me; and
"-c-d-" is —$CH_2$—C(O)—.

6. A compound according to claim 1 of structure IIa wherein
R is —OC(O)Me;
$R^3$ is H;
$R^5$ is H;
"-a-b-" is —O—$CH_2$—; and
"-c-d-" is —CH═CH—.

7. A compound according to claim 1 of structure IIb wherein
R is —OH;
$R^3$ is H;
$R^5$ is H;
"-a-b-" is —O—$CH_2$—; and
"-c-d-" is —$CH_2$—C(O)—.

8. A compound according to claim 1 of structure IIb wherein
R is —OH;
$R^3$ is H;
$R^5$ is H;
"-a-b-" is —O—$CH_2$—; and
"-c-d-" is —(O)C—$CH_2$—.

9. The compound according to claim 2 wherein
$R^1$ is H; and
"-c-d-" is CH(OH)—CH(OH).

10. The compound according to claim 2 wherein
$R^1$ is Ac;
"-c-d-" is —CH═CH—; and
$n=n_1=1$.

11. A compound according to claim 1 selected from

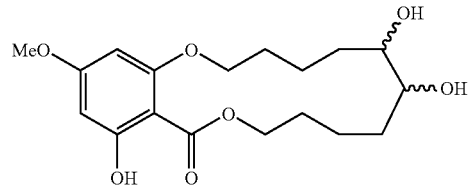

-continued
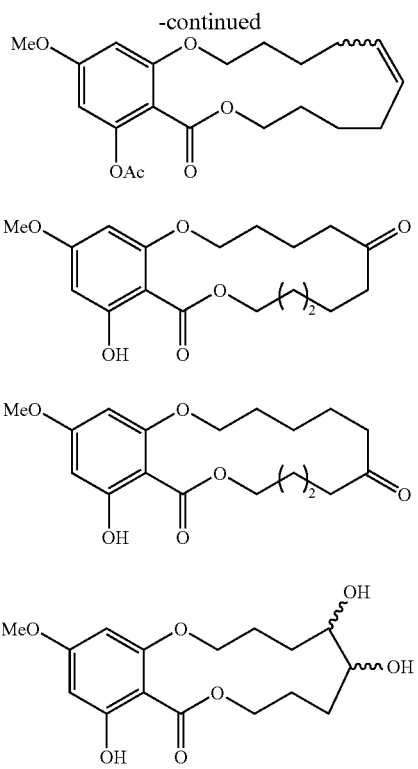
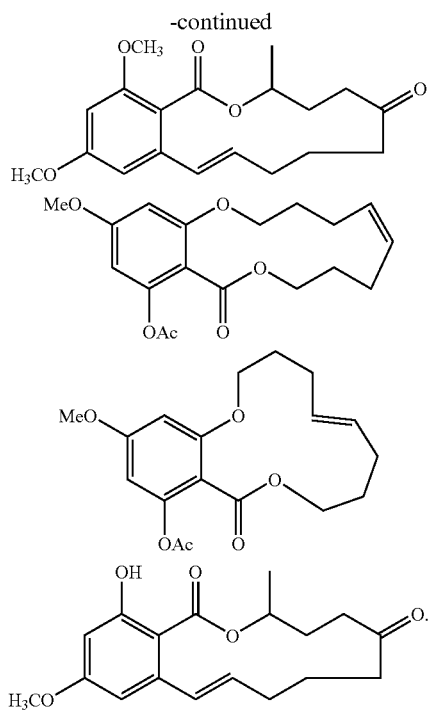
* * * * *

UNITED STATES PATENT AND TRADEMARK OFFICE
CERTIFICATE OF CORRECTION

PATENT NO. : 7,553,979 B2  Page 1 of 1
APPLICATION NO. : 10/496401
DATED : June 30, 2009
INVENTOR(S) : Srinivas R. Kasibhatla et al.

It is certified that error appears in the above-identified patent and that said Letters Patent is hereby corrected as shown below:

On the title page, item (75), line 4, "Iingleside," should read --Ingleside,--.

In claim 1, column 31, line 41, "a-b-" should read -- -a-b- --.

In claim 1, column 31, line 53, "ON," should read --CN,--.

In claim 1, column 31, line 55, "hydrogen" should read --hydrogen,--.

In claim 1, column 31, line 62, "N0$_2$," should read --NO$_2$,--.

In claim 11, column 34, lines 2-8, delete

" 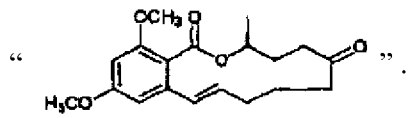 ".

In claim 11, column 34, lines 23-28, delete

" 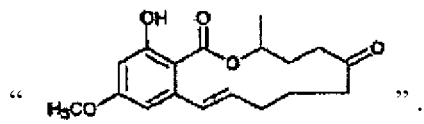 ".

Signed and Sealed this

Twenty-fifth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,553,979 B2 | Page 1 of 1 |
| APPLICATION NO. | : 10/496401 | |
| DATED | : June 30, 2009 | |
| INVENTOR(S) | : Kasibhatla et al. | |

It is certified that error appears in the above-identified patent and that said Letters Patent is hereby corrected as shown below:

On the Title Page

Item [*] Notice:   Subject to any disclaimer, the term of this patent is extended or adjusted under 35 USC 154(b) by 360 days Delete the phrase "by 360 days" and insert -- by 963 days --

Signed and Sealed this

Twenty-second Day of June, 2010

David J. Kappos
*Director of the United States Patent and Trademark Office*